United States Patent [19]

Egan et al.

[11] 4,362,388

[45] Dec. 7, 1982

[54] REMOTE MEASUREMENT OF CONCENTRATION OF A GAS SPECIE BY RESONANCE ABSORPTION

[75] Inventors: Walter D. Egan, Bethlehem; Roger T. Boos, Coopersburg, both of Pa.; Robert L. Byer, Stamford, Calif.; Richard K. DeFreez, Beaverton, Oreg.

[73] Assignee: Bethlehem Steel Corp., Bethlehem, Pa.

[21] Appl. No.: 207,850

[22] Filed: Nov. 17, 1980

[51] Int. Cl.³ .............................................. G01N 21/00
[52] U.S. Cl. ..................................... 356/341; 356/343
[58] Field of Search ............... 356/301, 318, 338, 341, 356/343, 435, 437; 250/343

[56] References Cited

U.S. PATENT DOCUMENTS 3,761,724  9/1973  Dennis .
3,766,380 10/1973  Menzies .
3,768,908 10/1973  Zaromb .
3,778,742  1/1974  Garbany .
3,820,901  6/1974  Kreuzer .
3,998,557 12/1976  Javan .

Primary Examiner—John K. Corbin
Assistant Examiner—Matthew W. Koren
Attorney, Agent, or Firm—Joseph J. O'Keefe; Michael J. Delaney

[57] ABSTRACT

The concentration of a selected gas specie at a situs determined by directing a laser beam at the situs, the beam including a wavelength within the resonance absorption band of the gas specie, and measuring the intensity of the laser beam energy scattered from two spaced volumes along said beam at the situs. The ratio of measured intensities is a relative measure of the concentration of the gas specie at the situs.

12 Claims, 3 Drawing Figures

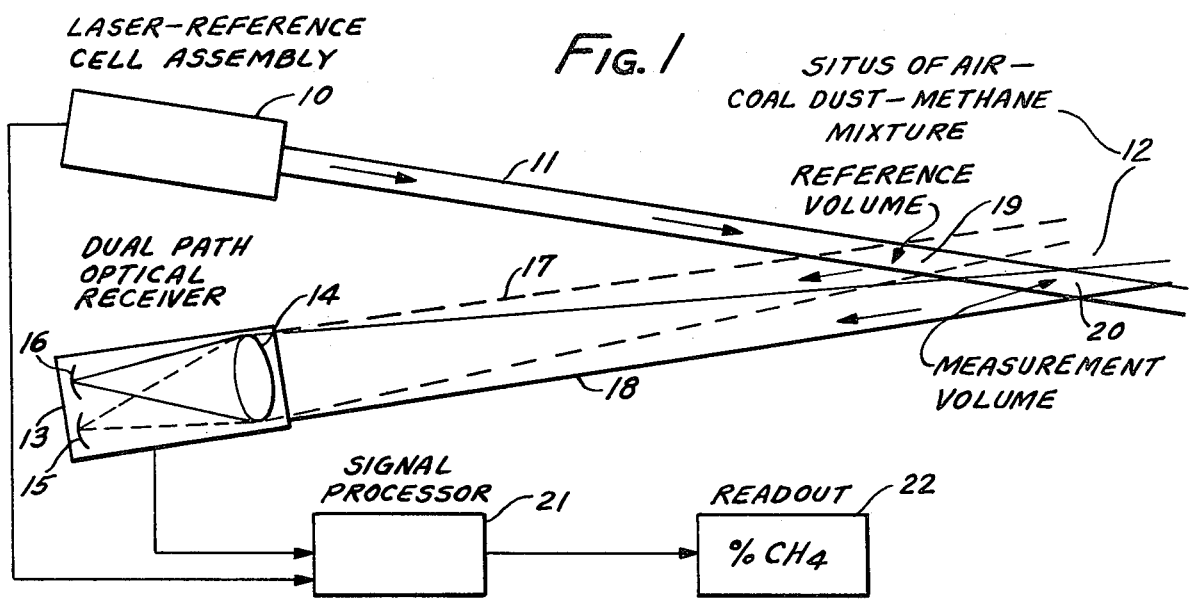
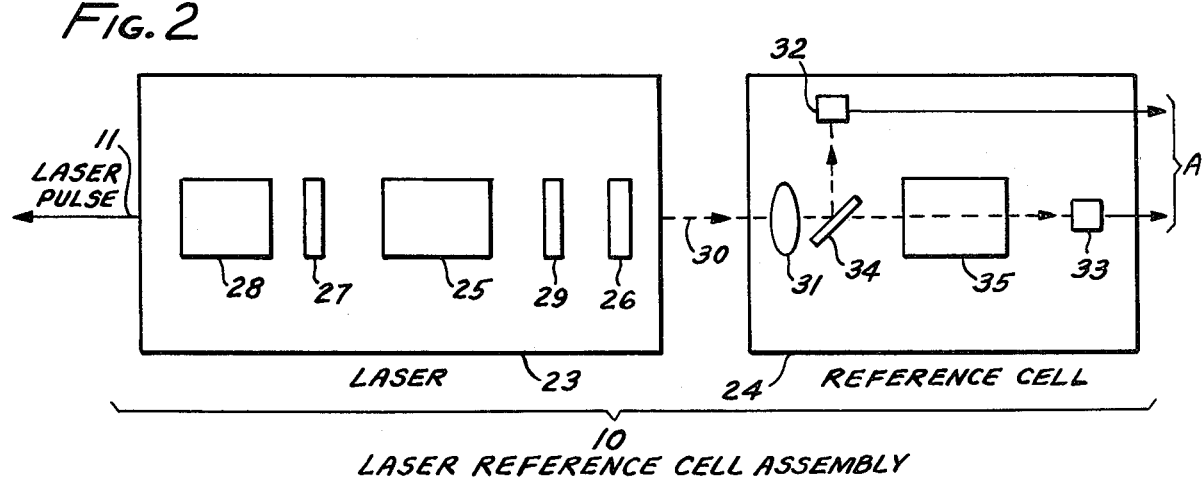
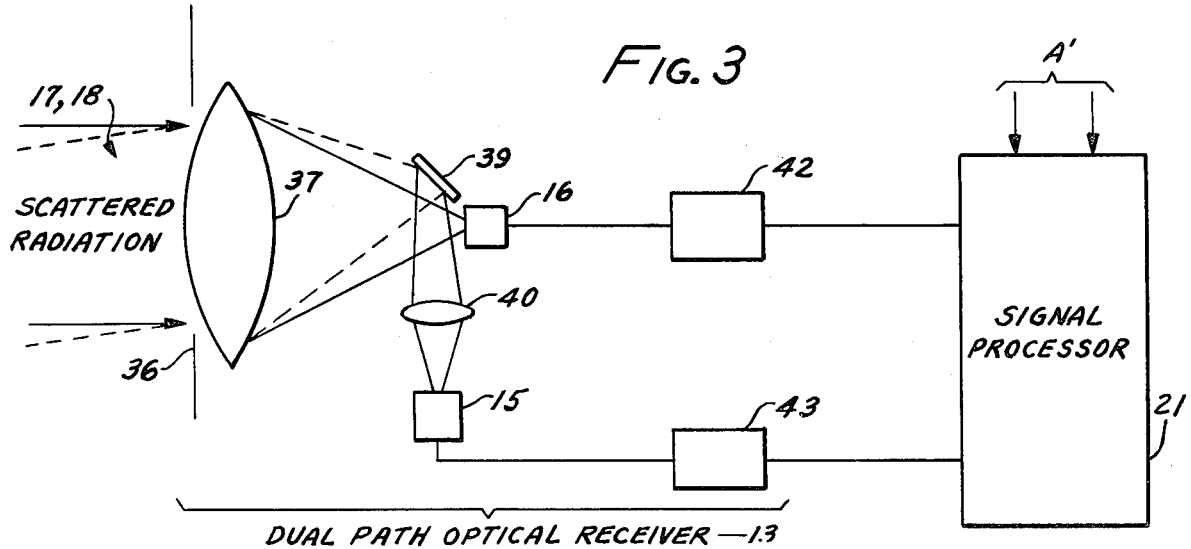

REMOTE MEASUREMENT OF CONCENTRATION OF A GAS SPECIE BY RESONANCE ABSORPTION

BACKGROUND AND SUMMARY OF INVENTION

The present invention relates generally to the detection and quantitative measurement of a selected gas specie. More particularly, this invention relates to said detection and measurement by the technique of selective resonance absorption of an energy frequency band characteristic of the gas specie. In accordance with the invention, an energy beam containing said band is transmitted from a remote source to the situs under test, and is then scattered to the same approximate area as the source. The degree of absorption of energy in said frequency band is measured to determine the concentration of said gas specie. This invention is described herein with specific reference to the detection of methane at a mine working face, but it will be apparent that the invention is limited neither to that gas specie nor to that environment, and may be readily adapted to the detection of other gas species in other environments, provided that the environment provides means for scattering of the energy beam.

It is well known that different gas species have different characteristic resonance absorption spectra, and this property has been used for the identification, detection and quantitative measurement of gases. The prior art discloses that methane can be detected in this way. For example, a Letter by White and Watkins in *Applied Optics*, vol. 14, no. 12, p. 2812 (Dec. 1975), discloses that an erbium:YAG laser emission centered at 1644.9 nm., overlaps the methane absorption line centered at 1645.1 nm., and suggests that this relation may be used to detect the presence and concentration of methane. The Letter further suggests the possibility of two differential absorption techniques for remote sensing of methane using the erbium:YAG laser—direct transmission measurement, and Mie scattering measurement. For such purpose it is suggested that in the process the laser radiation be tuned on and off the absorption frequency, to distinguish the energy absorption due to methane from attenuation due to other causes.

The use of selective resonance absorption to detect a gas specie, in a system utilizing laser energy and back-scattering of the energy, is disclosed in U.S. Pat. No. 2,788,742 to Max Garbuny. Other U.S. patent Nos. disclosing the general technique of selective frequency absorption of laser energy to detect the presence of a particular gas specie, are listed:

| | |
|---|---|
| 3,761,724 | James L. Dennis |
| 3,766,380 | Robert T. Menzies |
| 3,768,908 | Solomon Zaromb |
| 3,820,901 | Lloyd B. Kreuzer |
| 3,856,406 | Milton L. Noble et al; |
| 4,061,918 | Horst Preier et al. |

The present invention, as a methane detector, uses an erbium:YAG laser to generate a beam of energy that includes the methane resonance absorption band centered at 1645.1 nm.. The laser transmission is alternated between frequencies on and off said absorption band. One portion of the laser output is transmitted to the situs to be tested, while another portion is directed to a methane reference cell. Because of the environment at the situs to be analyzed, a portion of the laser energy reaching that area is back-scattered or reflected back or scattered toward the laser source.

Detection of the scattered energy is done off-axis of the source, by two spatially displaced detectors. Because of this geometry, the two detectors measure the reflected energy from two spaced volumes, one being referred to hereinafter as the reference volume and the other as the measurement volume. The energy path to and from one volume is greater than the path to and from the other volume. Because of the difference in path lengths, a basis for measuring methane concentration in a remote situs is established. The portion of the laser output directed through the methane reference cell is also detected. This latter measurement provides a reference that enables corrections or compensations in the measurement for small variations in laser frequency in the resonance absorption band.

From the data obtained by detection of the scattered energy from the spaced volumes, and the detection of the energy transmitted through the reference cell, utilizing laser frequencies shifted between on and off the gas specie absorption band, it is possible to compute the relative concentration of the absorbing gas specie, i.e. methane in the illustration being used. Referencing this relative concentration measurement to a predetermined calibration from known methane concentrations, the actual concentration of methane in the measurement volume can be determined.

Although the present invention is not limited to the detection of methane, and is not limited to any particular environment, it is contemplated that it will find an important application in the remote detection of methane at a coal mine working face. A coal mine working face usually has a high concentration of coal dust in the environment, and this provides a rather effective mechanism for scattering the laser energy. Because of the explosion hazard of both coal dust and methane, it is an important safety matter to be able quickly and readily to determine the methane concentration at a mine working face. Likewise, and for that very reason, it is most desirable to be able to make that determination from a remote location, with reasonable accuracy. It is expected that the present invention will fulfill those needs.

It is therefore the object of the present invention to provide for the remote detection and quantitative measurement of the concentration of a particular gas specie, utilizing the resonance absorption characteristics of the gas specie.

It is another object of the present invention to provide for said detection and measurement by irradiating the situs to be measured with energy including energy within said resonsance absorption band, and measuring the energy scattered from said situs.

Another object of the present invention is to provide for said detection and measurement as aforesaid, utilizing a laser as the source of said energy.

Still another object of the invention is to provide for said detection and measurement as aforesaid, wherein said laser frequency is switched between on and off the resonance absorption frequency band of the gas specie.

And still another object of the invention is to provide for said detection and measurement as aforesaid, and detecting the scattered energy at two spaced volumes.

And a further object of the invention is to provide for said detection and measurement, wherein said gas specie is methane.

And a still further object of the invention is to provide for said detection and measurement of methane at a mine working face.

Other objects and various advantages of the invention will become apparent to those skilled in the art, from a consideration of a description of a specific embodiment of the invention presented hereinafter.

DESCRIPTION OF THE DRAWINGS

The following description of a specific embodiment of the invention is had in conjunction with the accompanying drawings, wherein like reference characters refer to like or corresponding parts, and wherein:

FIG. 1 is a schematic showing of a system embodying the present invention;

FIG. 2 is a schematic showing of a laser and reference cell utilized in the system of FIG. 1; and FIG. 3 is a schematic showing of an optical receiver utilized in the system of FIG. 1.

DETAILED DESCRIPTION

The overall system of the present invention is illustrated in FIG. 1. As there depicted, a laser-reference cell assembly 10 emits a pulsed laser beam 11 into an area or situs 12 under test. In the particular embodiment, the situs 12 is intended to be near the working face of a coal mine at a distance of 20 to 40 feet, and therefore contains a rather significant concentration of coal dust (perhaps in the range of about 20 to 200 mg./m$^3$.). This atmosphere may also contain a significant concentration of methane (perhaps in the range of about 0.3 to 3.5%), and it is the purpose of this invention to measure the concentration of methane present.

Energy from the laser beam 11 is scattered by the coal dust in the situs depicted at 12 to the dual path optical receiver 13. In FIG. 1, the receiver 13 is shown as comprising a lens 14 focusing the reflected laser energy onto two spaced detectors 15 and 16. Because of the relative displacement of the detectors, they detect reflected energy from two slightly different directions. Detector 15 senses energy reflected along the beam 17 shown in dashed lines, while detector 16 senses energy reflected along the beam 18 shown in solid lines. Therefore, detector 15 measures the scattered laser energy from the reference volume 19 in the test situs 12, while detector 16 measures the scattered laser energy from the measurement volume 20 in the test situs 12. Measurement volume 20 is located farther from the optical receiver 13 than reference volume 19.

The outputs of the two detectors 15 and 16 are coupled to a signal processor 21. Likewise, the reference outputs of the laser detected from the laser directly and from a methane reference cell in the assembly 10, are coupled to signal processor 21. As will be explained subsequently, these inputs enable the signal processor 21 to develop a readout at 22 of the percent of methane in the environment at situs 12.

A detailed schematic of the laser-reference cell assembly 10, shown in FIG. 2, comprises the laser 23 and the reference cell 24. The laser 23 is well known, and comprises an erbium:YAG rod 25, a reflecting mirror 26, an output mirror 27, and a collimator 28, for generating the laser pulse beam 11. In addition, the laser includes an etalon 29. The nominal wavelength of the erbium:YAG laser is 1644.9 nm.. The etalon is used to tune the laser onto the methane absorption line of 1645.1 nm., and in operation the laser is scanned on and off the methane absorption frequency by tilting the etalon approximately 0.5 degree. A specific laser used for the present purpose produced a pulse rate of one pulse per 30 seconds, of approximately 1.5 milliseconds duration, and 2-3 millijoules. The frequency of scan between on and off the methane absorption frequency may correspond to the pulse frequency of the laser.

A portion of the laser output indicated at 30 is coupled into the reference cell 24. This laser energy is focused by an optical system indicated by lens 31 and beam splitter 34 on two detectors which may be pyroelectric detectors 32 and 33. A portion of beam 30 impinges directly on detector 32, while the portion of the beam 30 impinging on detector 33 first passes through a reference methane gas cell 35, containing a desired concentration of methane which is a function of the cell length and pressure of gas in the cell. A 6-inch long gas cell filled with methane gas to a pressure of about 120 mm. was used for the reference methane gas cell 35. The outputs of detectors 32 and 33 indicated at A are coupled at A′ (FIG. 3) to the signal processor 21. Thus, for each laser pulse, the portion of the energy indicated at 30 is measured before and after passing through methane cell 35. The ratio of these two measurements is used in the calculation with the test situs measurements to provide a compensation factor for changes in laser output frequency due to small positioning errors in the etalon tilt angle.

The dual path optical receiver 13 is shown in detailed schematic form in FIG. 3. The laser energy that is scattered from the test site 12 along paths 17 and 18, passes the optical aperture 36 into an optical system. The energy along path 18 from the measurement volume 20 (FIG. 1) is focused by the lens 37 directly on detector 16. The energy along path 17 from the reference volume 19 impinges upon mirror 39, and by means of lens 37 and lens 40 is focused on detector 15. Detectors 15 and 16 may be intrinsic germanium detectors. The outputs of these detectors 15 and 16 are coupled by preamplifiers 42 and 43 to the signal processor 21.

The electrical voltage signals obtained from the four detectors 32, 33, 15 and 16, in a system configured in the manner described hereinabove, provide the measurements, which in combination with the physical geometry, enable the calculation of a value related to the methane concentration at the test situs, in accordance with the following formula:

$$\% \text{ Concentration} = \frac{\ln\left[\frac{V_{on}(R2)}{V_{on}(R1)}\right] - \ln\left[\frac{V_{off}(R2)}{V_{off}(R1)}\right] C_R L}{2(R1 - R2) \ln\left[\frac{T_{off}}{T_{on}}\right]}$$

where
$V_{on}$ (R2) = measured voltage from the first detector for a laser pulse on the resonance absorption band scattered from the reference volume.
$V_{on}$ (R1) = measured voltage from the second detector for a laser pulse on the resonance absorption band scattered from the measurement volume.
$V_{off}$ (R2) = measured voltage from the first detector for a laser pulse off the resonance absorption band scattered from the reference volume.
$V_{off}$ (R1) = measured voltage from the second detector for a laser pulse off the resonance absorption band scattered from the measurement volume.

$C_R$ = percent concentration of the specie of gas in the reference cell.

$L$ = length in inches of the reference cell.

$(R1-R2)$ = distance in inches between the midpoints of the measurement volume and the reference volume.

$T_{off}$ = ratio of laser pulse energy off the resonance absorption band before and after transmission through the reference cell.

$T_{on}$ = ratio of laser pulse energy on the resonance absorption band before and after transmission through the reference cell.

The percent concentration of a gas specie calculated from the foregoing formula is a relative measure of the gas specie concentration at situs 12. The absolute or corrected concentration is obtainable by calibration of the instrument over a desired range from known concentrations of the gas specie.

From the foregoing illustrative embodiment, it will be appreciated that the present invention provides for the remote measurement of the concentration of a desired gas specie, such as methane, utilizing the resonance absorption characteristic of the gas specie, and scattering of energy by the environment at the situs of the gas under test. Basically, pursuant to the invention, one irradiates the situs under test with energy including the resonance absorption frequency of the gas specie of concern. Scattered energy is detected from two different optical axes designed to provide two spatially displaced volumes under examination at the test situs. With the total length of travel of the energy from the irradiating source to one detector being different from the length of travel to the other detector, a difference in degree of absorption of the energy by the gas specie is obtained as a result of the different lengths of traverse through the energy absorption medium. The ratio provided by this difference is the basis from which one may then calculate the concentration of the gas specie at the test situs. It is, of course, highly desirable to distinquish the absorption of energy as a result of the specific gas specie under investigation, and the general attenuation of the energy as results from other factors. Therefore, in the practice of the invention, it is contemplated that the irradiating energy be selectively (such as alternately) on and off the resonance absorption frequency of the gas specie under investigation. Thus, the off frequency irradiation provides a ratio indicative of the general attenuation factors.

It will thus become apparent to those skilled in the art that these basic concepts of the invention can be practiced with various modifications of the specific embodiment described. Such modifications as are embraced by the spirit and scope of the appended claims are contemplated as within the purview of the present invention.

We claim:

1. In a system for the remote measurement of the concentration of a gas specie at a situs, means for generating electromagnetic energy including a frequency within a resonance absorption band of said gas specie, means for forming said energy into a beam and directing it along an axis in said situs, means for detecting said energy including two spatially displaced detectors positioned off said axis, two spaced volume segments of said situs with one of said detectors measuring energy scattered from the first of said volume segments and the other of said detectors measuring energy scattered from the second of said volume segments, means for coupling said energy as scattered from said two spaced volume segments of said situs to said detecting means, and means for determining the relation of the intensities of the energy detected from said two spaced segments, said relation of energy intensities being indicative of the concentration of said gas specie at said situs.

2. In a system as set forth in claim 1, said coupling means defining two coupling paths, the first coupling path being from one of said detecting means to said first of said volume segments, and said second coupling path being from the other of said detecting means to said second of said volume segments, said two segments being spaced along said beam at said situs.

3. In a system as set forth in claim 1, said generating means generating energy selectively including and excluding a frequency within the resonance absorption band of said gas specie.

4. In a system for the remote measurement of the concentration of a gas specie at a situs, means for generating electromagnetic energy including a frequency within a resonance absorption band of said gas specie, means for forming said energy into a beam and directing it along an axis in said situs, means for detecting said energy including two spatially displaced detectors positioned off said axis, means for coupling said energy as scattered from two spaced volume segments of said situs to said detecting means, and means for determining the relation of the intensities of the energy detected from said two spaced segments, said relation of energy intensities being indicative of the concentration of said gas specie at said situs, said coupling means defining two coupling paths, the first coupling path being from said detecting means to a first of said volume segments, and said second coupling path being from said detecting means to a second of said volume segments, said two segments being spaced along said beam at said situs, one of said two spatially displaced detectors detects said energy along said first coupling path, and the other of said two spatially displaced detectors detects said energy along said second coupling path.

5. In a system as set forth in claim 4, one of said coupling paths being shorter than the other coupling path.

6. In a system as set forth in claim 4, said means for forming and directing said beam of energy comprising optical means, and said coupling means comprising a dual path optical receiver.

7. In a system as set forth in claim 6, said generating means comprising a laser means.

8. In a system for the remote measurement of the concentration of a gas specie at a situs, means for generating electromagnetic energy including a frequency within a resonance absorption band of said gas specie, means for forming said energy into a beam and directing it along an axis in said situs, means for detecting said energy including two spatially displaced detectors positioned off said axis, means for coupling said energy as scattered from two spaced volume segments of said situs to said detecting means, and means for determining the relation of the intensities of the energy detected from said two spaced segments, said relation of energy intensities being indicative of the concentration of said gas specie at said situs, said generating means generating energy selectively including and excluding a frequency within the resonance absorption band of said gas specie, said generating means comprising a laser, said coupling means comprising a dual path optical receiver, said spaced volume segments being along said beam and one of said two spatially displaced detectors detects said energy along one path of said receiver and the other detects said energy along the other path of said receiver.

9. In a system as set forth in claim 8, a reference cell containing said gas specie, means for directing a portion of said energy generated by said laser through said cell, means for detecting the intensity of said energy emerging from said cell, means for directly detecting the intensity of a portion of said energy generated by said laser, and means for determining the ratio of said last two intensities.

10. In a method of remotely determining the concentration of a specie of gas at a situs comprising, directing a beam of energy along an axis to said situs wherein said energy beam includes a frequency within a resonance absorption band of said specie of gas, detecting said energy by spatially displaced detectors positioned off said axis, measuring the intensities of the energy scattered from two spaced volumes along said beam at said situs with one of said detectors measuring said intensity from a first of said volumes and another of said detectors measuring said intensity from a second of said volumes, and determining the ratio of said intensities, said ratio being a measure of the concentration of said gas specie.

11. In a method of remotely determining the concentration of a specie of a gas at a situs comprising, directing a beam of energy along an axis to said situs wherein said energy beam includes energy frequencies on and off a resonance absorption band of said specie of gas, measuring the intensities of said energy frequencies scattered from a measurement volume and a reference volume along said beam at said situs by a first detector and a second detector spatially displaced from said first detector with said first detector and second detector positioned off said axis, measuring the intensity of a portion of said energy beam at said energy frequencies before and after it passes through a reference cell containing a sample of the gas specie, and determining the percent concentration of said specie of gas using the following formula:

$$\% \text{ Concentration} = \frac{\ln\left[\frac{V_{on}(R2)}{V_{on}(R1)}\right] - \ln\left[\frac{V_{off}(R2)}{V_{off}(R1)}\right] C_R L}{2(R1 - R2) \ln\left[\frac{T_{off}}{T_{on}}\right]}$$

where $V_{on}(R2)$ = measured voltage from the first detector for a laser pulse on the resonance absorption band scattered from the reference volume $V_{on}(R1)$ = measured voltage from the second detector for a laser pulse on the resonance absorption band scattered from the measurement volume $V_{off}(R2)$ = measured voltage from the first detector for a laser pulse off the resonance absorption band scattered from the reference volume $V_{off}(R1)$ = measured voltage from the second detector for a laser pulse off the resonance absorption band scattered from the measurement volume $C_R$ = percent concentration of the specie of gas in the reference cell L = length in inches of the reference cell (R1-R2) = distance in inches between the midpoints of the measurement volume and the reference volume $T_{off}$ = ratio of laser pulse energy off the resonance absorption band before and after transmission through the reference cell $T_{on}$ = ratio of laser pulse energy on the resonance absorption band before and after transmission through the reference cell 12. In a method as set forth in claim 11, said specie of gas being methane.

* * * * *